(12) United States Patent
Stefanchik

(10) Patent No.: US 8,357,170 B2
(45) Date of Patent: Jan. 22, 2013

(54) DEVICES AND METHODS FOR PLACING OCCLUSION FASTENERS

(75) Inventor: David Stefanchik, Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 961 days.

(21) Appl. No.: 12/170,126

(22) Filed: Jul. 9, 2008

(65) Prior Publication Data

US 2010/0010510 A1    Jan. 14, 2010

(51) Int. Cl.
*A61B 17/10* (2006.01)
(52) U.S. Cl. .................. 606/142; 606/139; 606/143
(58) Field of Classification Search .............. 606/139, 606/142, 143
See application file for complete search history.

(56) References Cited

U.S. PATENT DOCUMENTS

| | | | | |
|---|---|---|---|---|
| 4,791,707 A | * | 12/1988 | Tucker | 227/19 |
| 4,854,317 A | * | 8/1989 | Braun | 606/143 |
| 5,035,692 A | * | 7/1991 | Lyon et al. | 606/143 |
| 5,100,418 A | | 3/1992 | Yoon et al. | |
| 5,156,609 A | | 10/1992 | Nakao et al. | |
| 5,174,276 A | * | 12/1992 | Crockard | 600/104 |
| 5,192,288 A | * | 3/1993 | Thompson et al. | 606/143 |
| 5,222,961 A | * | 6/1993 | Nakao et al. | 606/143 |
| 5,342,373 A | | 8/1994 | Stefanchik et al. | |
| 5,392,978 A | * | 2/1995 | Velez et al. | 227/177.1 |
| 5,395,381 A | * | 3/1995 | Green et al. | 606/143 |
| 5,433,721 A | | 7/1995 | Hooven et al. | |
| 5,474,567 A | | 12/1995 | Stefanchik et al. | |
| 5,601,573 A | * | 2/1997 | Fogelberg et al. | 606/143 |
| 5,601,574 A | | 2/1997 | Stefanchik et al. | |
| RE35,525 E | * | 6/1997 | Stefanchik et al. | 606/142 |
| 5,681,330 A | * | 10/1997 | Hughett et al. | 606/143 |
| 5,725,542 A | * | 3/1998 | Yoon | 606/157 |
| 5,730,740 A | | 3/1998 | Wales et al. | |
| 5,833,700 A | * | 11/1998 | Fogelberg et al. | 606/158 |
| 5,858,018 A | * | 1/1999 | Shipp et al. | 606/142 |
| 5,904,693 A | * | 5/1999 | Dicesare et al. | 606/143 |
| 5,921,997 A | | 7/1999 | Fogelberg et al. | |
| 5,993,465 A | * | 11/1999 | Shipp et al. | 606/142 |
| 6,139,555 A | * | 10/2000 | Hart et al. | 606/139 |
| 6,350,269 B1 | * | 2/2002 | Shipp et al. | 606/143 |
| 6,652,539 B2 | * | 11/2003 | Shipp et al. | 606/143 |
| 6,716,226 B2 | | 4/2004 | Sixto, Jr. et al. | |
| 6,743,240 B2 | | 6/2004 | Smith et al. | |
| 6,749,560 B1 | * | 6/2004 | Konstorum et al. | 600/143 |
| 6,824,548 B2 | | 11/2004 | Smith et al. | |
| 6,843,794 B2 | | 1/2005 | Sixto, Jr. et al. | |

(Continued)

FOREIGN PATENT DOCUMENTS

| | | |
|---|---|---|
| EP | 1468653 A2 | 10/2004 |
| WO | 03034928 A1 | 5/2003 |

OTHER PUBLICATIONS

International Search Report, PCT/US2009/049907, Mailed Aug. 28, 2009.

*Primary Examiner* — Dianne Dornbusch

(57) ABSTRACT

Methods and devices are provided for placing occlusion fasteners. In general, a surgical instrument is provided having a shaft configured to be introduced into a body through a scoping device and to deliver a ligating clip to occlude tissue in the body. The scoping device and the shaft can each be flexible, with the shaft configured to be advanced through a working channel of the scoping device. The shaft can have a size configured to allow a plurality of surgical instruments to be concurrently disposed in the scoping device's working channel and for one or more of the surgical instruments to extend beyond a distal end of the scoping device.

21 Claims, 12 Drawing Sheets

U.S. PATENT DOCUMENTS

| | | |
|---|---|---|
| 6,945,979 B2 | 9/2005 | Kortenbach et al. |
| 7,070,602 B2 | 7/2006 | Smith et al. |
| 7,090,685 B2 | 8/2006 | Kortenbach et al. |
| 7,105,000 B2 | 9/2006 | McBrayer |
| 7,223,272 B2 | 5/2007 | Francese et al. |
| 7,232,445 B2 | 6/2007 | Kortenbach et al. |
| 7,331,968 B2 | 2/2008 | Arp et al. |
| 7,357,806 B2 | 4/2008 | Rivera et al. |
| 7,367,939 B2 | 5/2008 | Smith et al. |
| 2002/0068945 A1 | 6/2002 | Sixto et al. |
| 2002/0078967 A1 | 6/2002 | Sixto et al. |
| 2002/0138086 A1* | 9/2002 | Sixto et al. ............ 606/151 |
| 2002/0198541 A1* | 12/2002 | Smith et al. ............ 606/142 |
| 2004/0097972 A1* | 5/2004 | Shipp et al. ............ 606/142 |
| 2004/0116948 A1 | 6/2004 | Sixto et al. |
| 2004/0193185 A1* | 9/2004 | McBrayer ............ 606/142 |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2005/0033333 A1 | 2/2005 | Smith et al. |
| 2005/0090837 A1 | 4/2005 | Sixto et al. |
| 2005/0090838 A1 | 4/2005 | Sixto et al. |
| 2005/0125010 A1 | 6/2005 | Smith et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2006/0217742 A1 | 9/2006 | Messerly et al. |
| 2006/0217743 A1 | 9/2006 | Messerly et al. |
| 2007/0296365 A1 | 12/2007 | Messerly et al. |
| 2008/0004622 A1 | 1/2008 | Coe et al. |

* cited by examiner

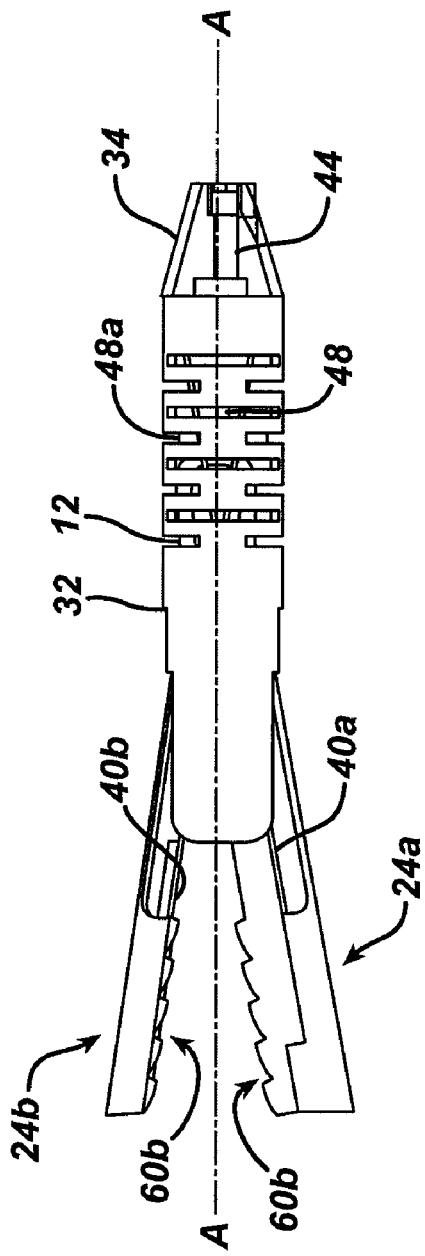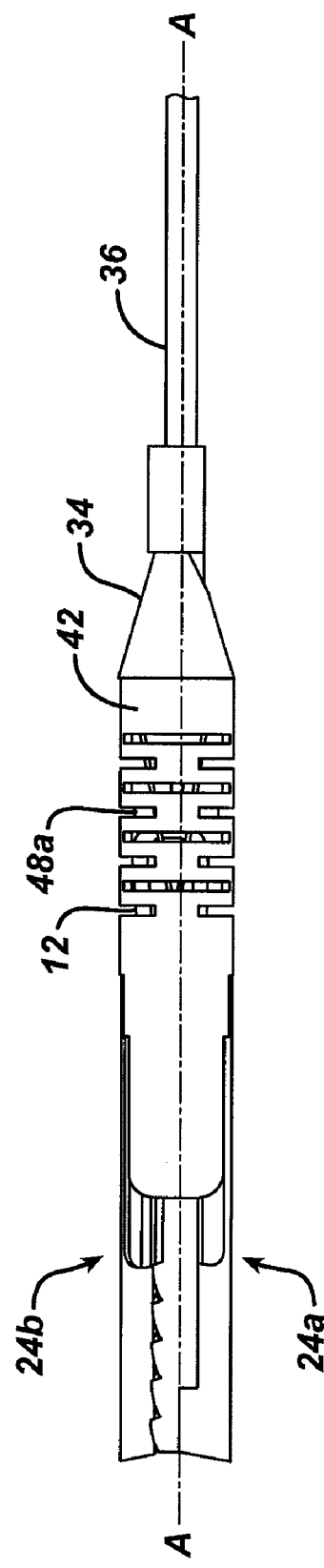

DEVICES AND METHODS FOR PLACING OCCLUSION FASTENERS

FIELD OF THE INVENTION

The present invention relates to methods and devices for placing surgical fasteners used to occlude bodily tissue structures, and in particular to methods and devices for ligating tissue using surgical clips.

BACKGROUND OF THE INVENTION

In order to prevent excessive fluid loss or bleeding during a surgical procedure, a surgeon can ligate or close various fluid ducts and/or blood vessels before severing those vessels. There are many types of mechanisms or devices for shutting off the vessels such as ligating clips, hemostatic clips, and the like. In some instances the surgeon will tie a ligature or suture about a vessel to close or shut the vessel. Ligating clips are well known in the art. Many of the clips are metal and comprise a pair of legs which are connected at one end. The vessel to be ligated is placed between the legs and the legs are forced together about the vessel to close the vessel. Clips have also been developed from plastic materials. However, since plastics do not have the same strength and malleability characteristics as metals, the plastic clips typically include some type of locking mechanism so that when the legs are urged together about the vessel they are locked in a closed position.

Ligating clips should ensure closure of the vessel. That is, they should completely shut off blood flow or other fluid flow and not allow leakage. Also, the clips should remain closed, should not open or break, and should not slip or slide out of position or off the vessel. While it does not take much force to collapse and close a vessel, some clips can require substantial force to close or change configuration so that once closed, the clip will remain in its closed position.

In minimally invasive surgery, in particular, endoscopic surgery, it has become desirable to provide smaller instruments capable of reaching surgical sites through smaller access ports. Smaller incisions cause less damage in accessing the surgical site and the access wounds from such incisions heal faster. The size of the instrument is dictated, in general, by the size of the clip as it is passed through the clip applying instrument to its business end and the size of the jaws used to crush the clips closed. Clips are typically passed through the clip applying instrument in an open position so as to allow the clip to capture a tissue structure to be ligated before the jaws crush the clip closed over the structure.

In endoscopic surgery, the business end of the instrument is placed within the body through an appropriate cannula, body canal, or small incision. The manipulation of that business end by the surgeon is accomplished outside the body. As a result, it becomes more difficult to control the business end of the instrument since it is further removed from the actual operation of the instrument. Any slight movement in the manipulation of the instrument outside the body is magnified at the business end of the instrument. Therefore, there is a greater chance in an endoscopic procedure that a slight movement of a clip applier as a clip is being closed will cause clip misplacement. This is particularly true considering that clips can require high force to effectively form over a tissue structure.

SUMMARY OF THE INVENTION

In general, methods and devices are provided for placing sterile occlusion fasteners. In one aspect, a surgical method is provided that includes advancing a clip applying device with a ligating clip removably disposed therein through a working channel of a flexible scoping device, wherein a distal end of the scoping device is disposed within a body of a patient, advancing the clip applying device through the scoping device to position a distal end of the clip applying device beyond the distal end of the scoping device, and advancing the clip through the clip applying device, with the distal end of the clip applying device positioned beyond the distal end of the scoping device, to clip tissue within the body of the patient with the clip. The clip has a folded configuration with a lower leg member of the clip located between an upper leg member of the clip and a connector portion of the clip. The connector portion extends between the upper and lower leg members.

The method can have any number of variations. In one embodiment, advancing the clip can include actuating a handle coupled to the clip applying device and positioned outside the body of the patient. As another variation, the method can include advancing at least one surgical instrument (e.g., a clip applying device, a tissue manipulating device, etc.) through the working channel while the clip applying device is disposed therein. As still another variation, the method can include disposing the scoping device within the body of the patient through a natural orifice.

In another aspect, a surgical method is provided that includes advancing a flexible surgical instrument through a working channel of a flexible scoping device at least until a distal end of the surgical instrument extends beyond a distal end of the scoping device, wherein the distal end of the scoping device is disposed in a patient, compressing a tissue of the patient between a pair of jaw members located at the distal end of the surgical instrument, advancing a ligating clip removably disposed in the surgical instrument through the surgical instrument and into the jaw members, and advancing the clip beyond the distal end of the surgical instrument and out of the jaw members, thereby moving the clip to the closed position with tissue clipped between the opposed tissue ligating surfaces of the clip. The jaw members are movable relative to a longitudinal axis of the surgical instrument. The clip is biased to a closed position and has opposed tissue ligating surfaces, and the jaw members apply a force to the clip against the bias of the clip to allow tissue compressed between the jaw members to be positioned between the opposed tissue ligating surfaces of the clip.

The jaw members and the clip can each have a variety of configurations. In one embodiment, the jaw members each have a sloped surface, the sloped surfaces engaging the clip and applying a force to the clip to pry apart the opposed tissue ligating surfaces of the clip. As another example, the jaw members can be in a closed position when the surgical instrument is advanced through the working channel, and when the jaw members extend beyond the distal end of the scoping device, the jaw members can move to an open position.

The method can include any number of variations. For example, the method can include advancing the surgical instrument through the working channel of the scoping device during a therapeutic surgical procedure. As another example, advancing the clip through the surgical instrument can include rotating a handle coupled to the surgical instrument and positioned outside the patient. As still another example, compressing the tissue of the patient between the jaw members can include rotating a handle coupled to the surgical instrument and positioned outside the patient. As another example, the method can include advancing at least one additional surgical instrument through the working channel while the surgical instrument is disposed therein at least until a distal end of the at least one additional surgical instrument extends beyond the distal end of the scoping device. As yet another example, compressing the tissue between the jaw members can include manually moving the jaw members from the open position to the closed position.

In another aspect, a surgical device is provided that includes a flexible shaft configured to be advanced through a flexible scoping device and to have a ligating clip in a closed position removably disposed therein. The shaft includes an outer tube with jaws at a distal end thereof, the jaws configured to move between open and closed positions, an inner tube disposed within the outer tube and configured to be movable to move the jaws between the open and closed positions, and a clip applying mechanism disposed within the inner tube and configured to be movable to advance the ligating clip beyond a distal end of the shaft. The ligating clip is configured to move to a closed position and clip tissue when advanced beyond the distal end of the shaft and when the jaws are in a closed position.

The shaft can be composed from a variety of materials. In one embodiment, the shaft can be composed of at least one of a shape memory material, stainless steel, and spring steel. For example, the shaft can be composed of a superelastic material, e.g., Nitinol.

The shaft can have any size, shape, and configuration. For example, the shaft can be non-coiled. As another example, the shaft can deliver about 15 pounds of push-pull force without deforming. As still another example, the shaft can achieve a radius of curvature of about 3 inches. As another example, the shaft can have a maximum diameter of about 1 mm. As yet another example, the shaft can be configured to have a plurality of ligating clips disposed therein, each of the plurality of ligating clips disposed therein in a closed position and configured to move from the closed position to an open position and back to the closed position to clip tissue when advanced beyond the distal end of the shaft and when the jaws are in a closed position, and the clip applying mechanism can be configured to sequentially advance each of the plurality of clips beyond the distal end of the shaft.

The ligating clip be composed of a variety of materials and have any size, shape, and configuration. In one embodiment, the ligating clip can be configured to advance through the jaws and to spring to a closed position to clip tissue when advanced beyond a distal end of the jaws.

The inner tube, the outer tube, the ligating clip, the scoping device, and the jaw members can also be composed of a variety of materials and have any size, shape, and configuration. For example, the inner tube can be configured to be axially movable with respect to the outer tube. As another example, the ligating clip can be configured to advance through the jaws and to spring to a closed position to clip tissue when advanced beyond a distal end of the jaws. As still another example, the scoping device can include one of an endoscope, a laparoscope, and a colonoscope. As another example, the jaws can include two jaw members, each of the jaw members configured to be movable with respect to a longitudinal axis of the outer tube.

The surgical device can have any number of variations. In one embodiment, the device can include a handle coupled to the shaft and configured to be actuated to move the inner tube and to move the clip applying mechanism. The handle can be configured to be actuated in a first actuating stroke to move the inner tube and in a second actuating stroke after the first actuating stroke to move the clip applying mechanism. The first actuating stroke can move the jaws from an open position to a closed position, thereby causing tissue to be compressed between tissue compressing surfaces of the jaws, and the second actuating stroke can advance the ligating clip over the tissue compressed between the tissue compressing surfaces to allow the ligating clip to move to a closed position to clip the tissue therebetween.

BRIEF DESCRIPTION OF THE DRAWINGS

The invention will be more fully understood from the following detailed description taken in conjunction with the accompanying drawings, in which:

FIG. 4 is a side schematic view of a distal portion of the clip applying device of FIG. 1 with a ligating clip disposed therein and the device's jaws in an open position;

FIG. 5 is a side schematic view of the clip applying device of FIG. 4 with the device's jaws in a closed position;

DETAILED DESCRIPTION OF THE INVENTION

Figure 1:
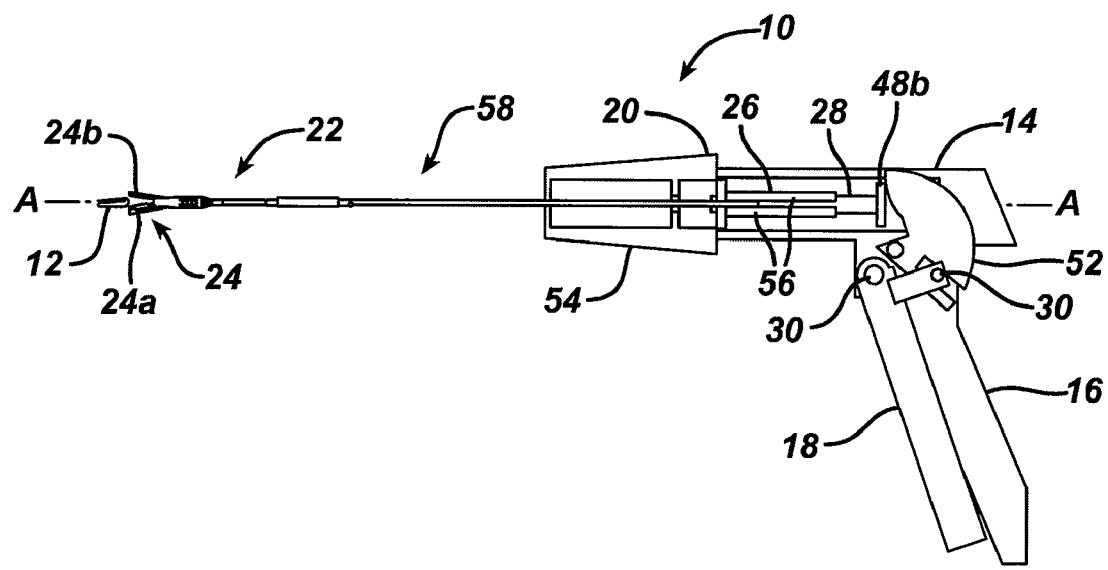
FIG. 1 is a schematic, cross-sectional view of an embodiment of a clip applying device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for placing occlusion fasteners. While the methods and devices disclosed herein can be used in conventional, open surgical procedures, they are particularly useful in minimally invasive surgical procedures, particularly laparoscopic surgery and endoscopic procedures. The surgical procedure can be diagnostic, e.g., a procedure generally undertaken to identify a medical condition, and/or therapeutic, e.g., a procedure generally undertaken to treat an identified medical condition. In addition, the particular types of tools described herein can be used alone in a surgical procedure, or they can be used in conjunction with other devices that facilitate minimally invasive surgical procedures. A person skilled in the art will appreciate that the present invention has application in conventional endoscopic and open surgical instrumentation as well application in robotic-assisted surgery.

In general, a surgical instrument is provided having a shaft configured to be introduced into a body through a scoping device and to deliver a ligating clip to occlude tissue in the body. While the clip can be used to occlude any tissue, in an exemplary embodiment the clip is configured for use in ligating a blood vessel. A person skilled in the art will appreciate that the term "tissue" as used herein is intended to encompass a variety of materials, e.g., blood vessels, body lumens, and any other material that needs to be occluded in a surgical procedure. A person skilled in the art will also appreciate that the scoping device can include any surgical tool having a cannula or other working channel through which the shaft of the surgical instrument can be advanced and that is configured to be inserted into a body, such as through a natural orifice, through a puncture hole formed in tissue, and in any other way appreciated by a person skilled in the art. Non-limiting examples of the scoping device include an endoscope, a laparoscope, and a colonoscope. While the scoping device can be rigid or flexible, in an exemplary embodiment, the scoping device is flexible.

In an exemplary embodiment, the shaft can be flexible to allow the shaft to be introduced into a body of a patient through a working channel of a flexible scoping device having at least its distal end disposed in the body. The shaft can be configured to have a ligating clip pre-loaded therein in a closed position, and the clip can also be introduced into the body through the scoping device's working channel. The clip can be deployed in the body using a control mechanism, e.g., a handle, at a proximal end of the shaft located outside the patient's body to ligate tissue during a surgical procedure. The shaft can be configured to have a plurality of clips disposed therein, and each of the clips can be deployed from the shaft to ligate tissue without requiring the shaft to be removed from the body between clip deployments.

In an exemplary embodiment, the shaft includes a solid tubing, e.g., is non-coiled, having a smooth and/or textured outside surface. Generally, a solid tube can transmit torque more effectively than a coil, e.g., spiral-bound wire, and thereby, e.g., help decrease a force necessary to manipulate the shaft and reduce distortion in the device's distal portion when rotating or otherwise manipulating the device from its proximal portion.

Figure 20:
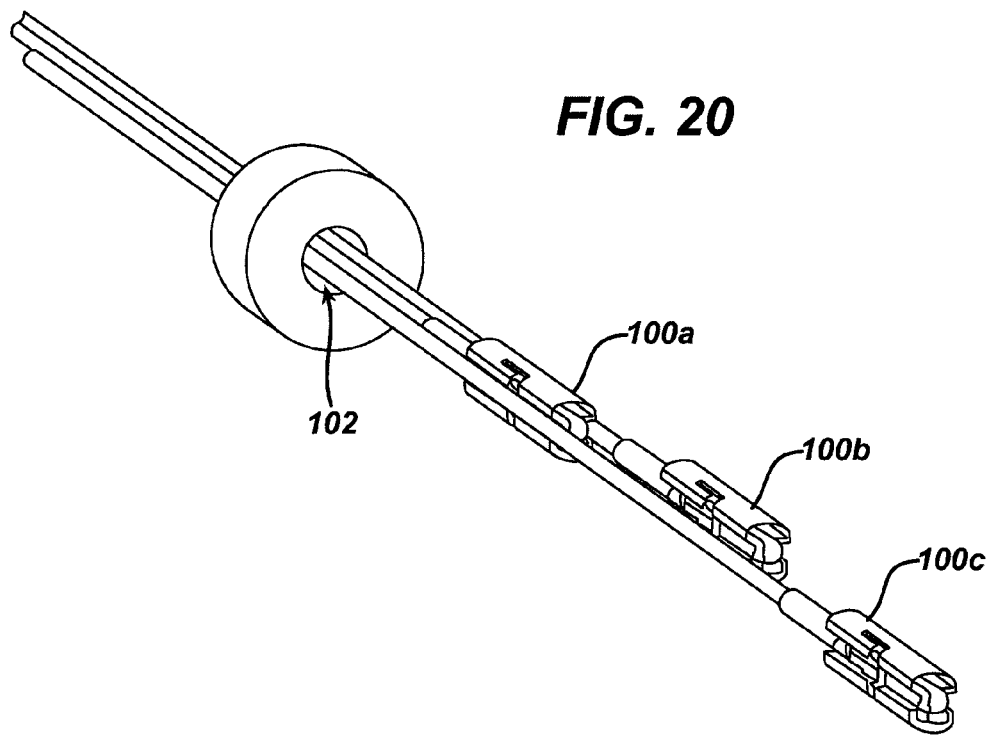
FIG. 20 is a perspective view of three clip applying devices advanced through a working channel of a surgical instrument.
Figure 21:
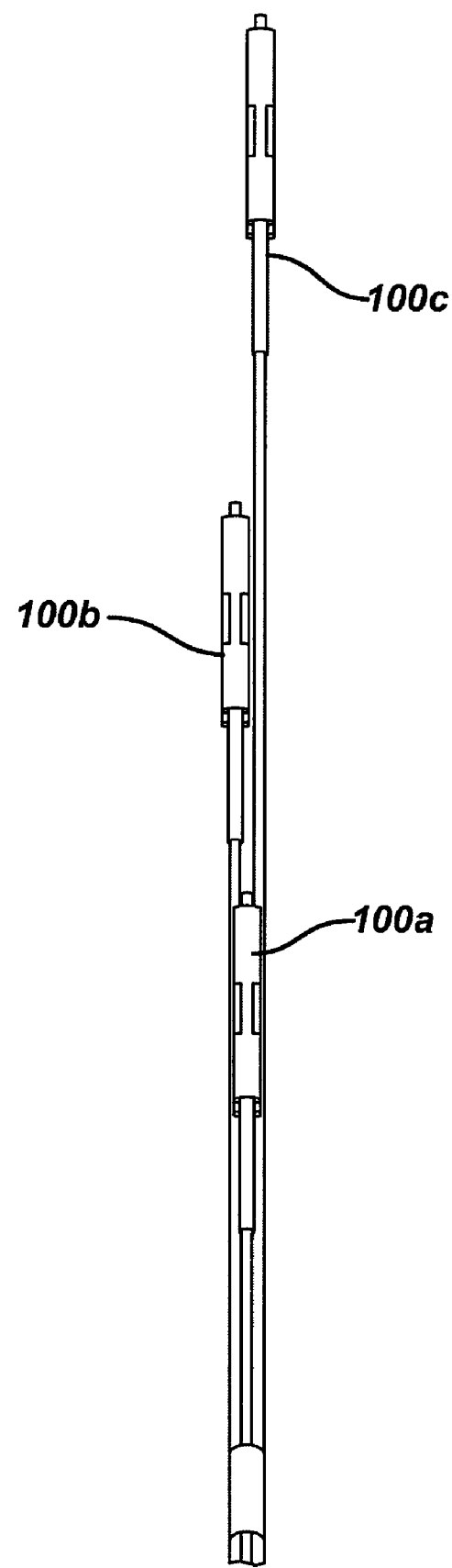
FIG. 21 is a top view of the three clip applying devices of FIG. 20 advanced through a working channel of a surgical instrument.
Figure 22:
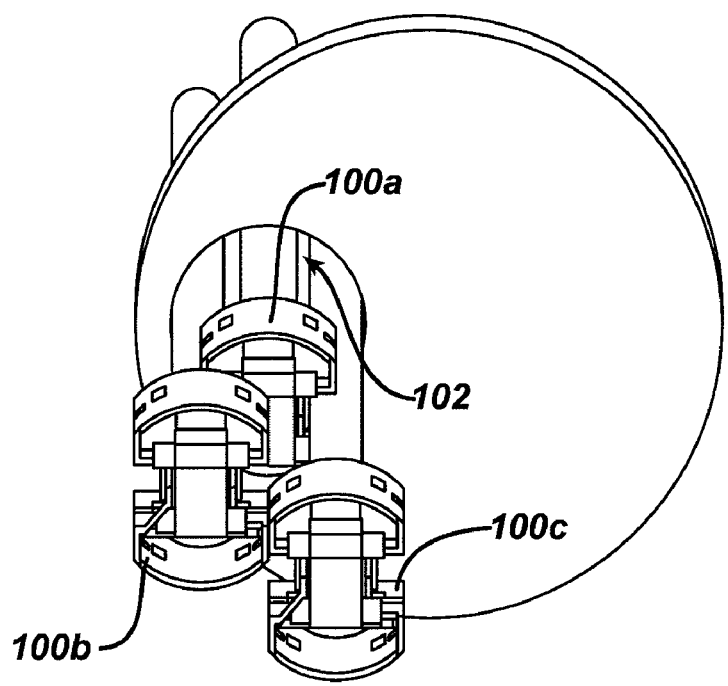
FIG. 22 is a perspective front view of the three clip applying devices of FIG. 20 advanced through a working channel of a surgical instrument.

In an exemplary embodiment the shaft has a substantially cylindrical shape and has a maximum diameter of about 1 mm, but the shaft can have any size and shape. Conventional scoping device working channels have a diameter of about 3.7 mm, and a shaft having a diameter less than or equal to 1 mm can easily be disposed within the working channel. Having a maximum diameter less than one-third the diameter of the scoping device's working channel can allow one or more additional surgical instruments to be disposed in the scoping device's working channel with the shaft concurrently disposed therein and for any one or more of those surgical devices to be advanced beyond a distal end of the scoping device. As illustrated in an exemplary embodiment shown in FIGS. 20-22, a surgeon can thus simultaneously introduce multiple surgical instruments (e.g., two, three, etc.) 100a, 100b, 100c into a patient's body at substantially the same location at a surgical site using the same working channel 102 of an introducer device and thereby allow concurrent use of those surgical instruments 100a, 100b, 100c, which can be particularly useful in endoscopic surgery where introducing and removing a scoping device can be a time-consuming, difficult process if the scoping device passes through a curved and/or delicate body structure, e.g., the gastrointestinal tract, the respiratory tract, etc. For non-limiting example only, a plurality of identical shafts (e.g., two, three, etc.) each having a maximum diameter of about 1 mm can fit in the same working channel at the same time. For another non-limiting example, a tissue manipulating device (e.g., grasper, forceps, tongs, retractor, etc.) having a maximum diameter of less than about 2.7 mm can be disposed in a 3.7 mm working channel concurrent with the shaft, e.g., to allow the tissue manipulator to manipulate tissue in the body while a clip is being applied to the manipulated tissue and/or to other tissue. Any combination of surgical instruments (e.g., shafts, tissue manipulators, etc.) can be introduced through the scoping device's working channel.

The devices discussed herein can be made from any combination of rigid and/or flexible materials, and in an exemplary embodiment, the materials are biocompatible. A person skilled in the art will appreciate that the term "flexible" as used herein is intended to encompass a variety of configurations. Generally, a "flexible" member has some degree of elasticity, e.g., is capable of bending without breaking.

In an exemplary embodiment, the shaft is composed of at least one biocompatible and flexible material, e.g., a shape memory material, stainless steel, spring steel, etc. Non-limiting examples of shape memory materials include a copper-zinc-aluminum-nickel alloy, a copper-aluminum-nickel alloy, a nickel-titanium alloy, a superelastic or pseudoelastic material (e.g., a material that does not require application of heat to return to its original shape following deformation), Nylon, Nylon blends, Veriflex™, etc. In an exemplary embodiment, the shaft is composed of the shape memory material Nitinol (a nickel-titanium alloy that is superelastic).

The ligating clip can include any ligating clip configured to occlude tissue, as will be appreciated by a person skilled in the art. Ligating clips are generally commercially available in a variety of sizes, e.g., small, medium, medium/large, and large, and any size of clip can be used with the clip applying device. The ligating clip can be composed of any one or more well-known materials as will be appreciated by a person skilled in the art, e.g., titanium, tantalum, stainless steel, a shape memory material, plastic (e.g., polyolefin, a glycolide-lactide polymer, etc.), etc. The yield strength of the ligating clip material can be sufficient to allow opening by the clip applying device of the clip, as discussed further below, to place it over tissue and resiliently return to its original (biased) closed position. In an exemplary embodiment, the ligating clip is composed of a titanium alloy, e.g., titanium 3Al-2.5V.

FIGS. 1-7 illustrate a surgical device 10 configured to deliver and apply a ligating clip 12 to a tissue at a surgical site in a body of a patient. A housing 14 includes a stationary handle 16, a trigger handle 18 movably mounted, e.g., pivotably, rotatably mounted, to the housing 14, and one or more mechanisms disposed within and/or coupled to the housing 14 configured to help effect movement of elements at a distal end of the device 10 as discussed further below. Such mechanisms can include an inner tube 20, an outer tube 26, and a clip applying mechanism 28. The outer tube 26 can be disposed within the housing 14 and configured to be movable to move jaws 24 including lower and upper jaw members 24a, 24b at a distal end 22 of the device 10. The inner tube 20 can be attached to a distal end of the housing 14, be disposed within the outer tube 26, and be configured to be movable via actuation of the trigger handle 18 to move the jaw members 24a, 24b. The clip applying mechanism 28 can be disposed within the inner tube 20 and the housing 14 and be configured to be movable via actuation of the trigger handle 18 to advance the clip 12 through the device 10.

Figure 2:
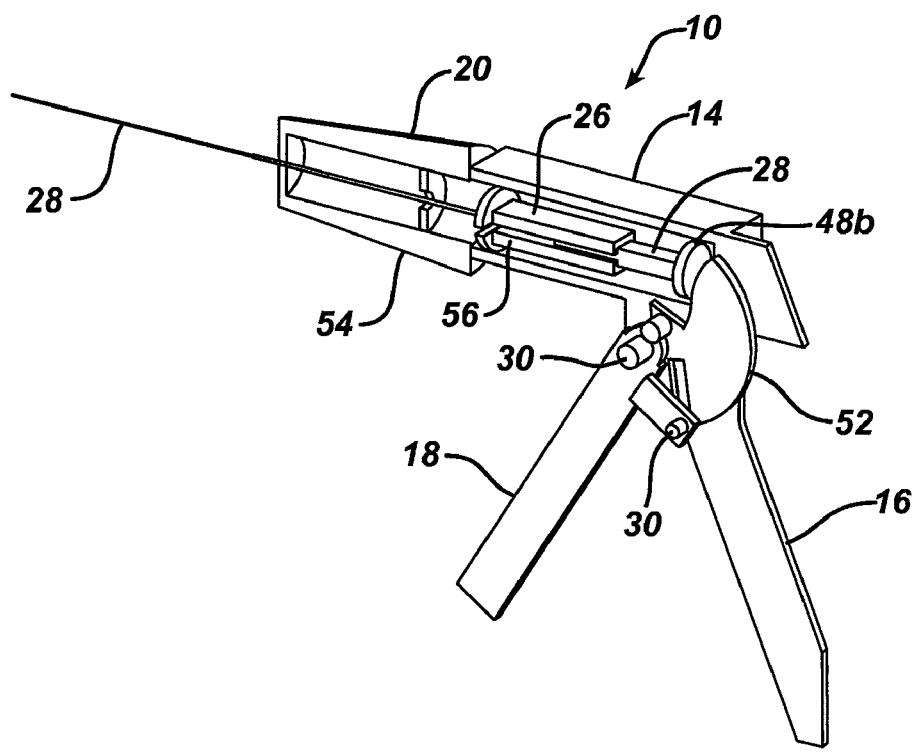
FIG. 2 is a partial perspective, cross-sectional view of the clip applying device of FIG. 1.
Figure 3:
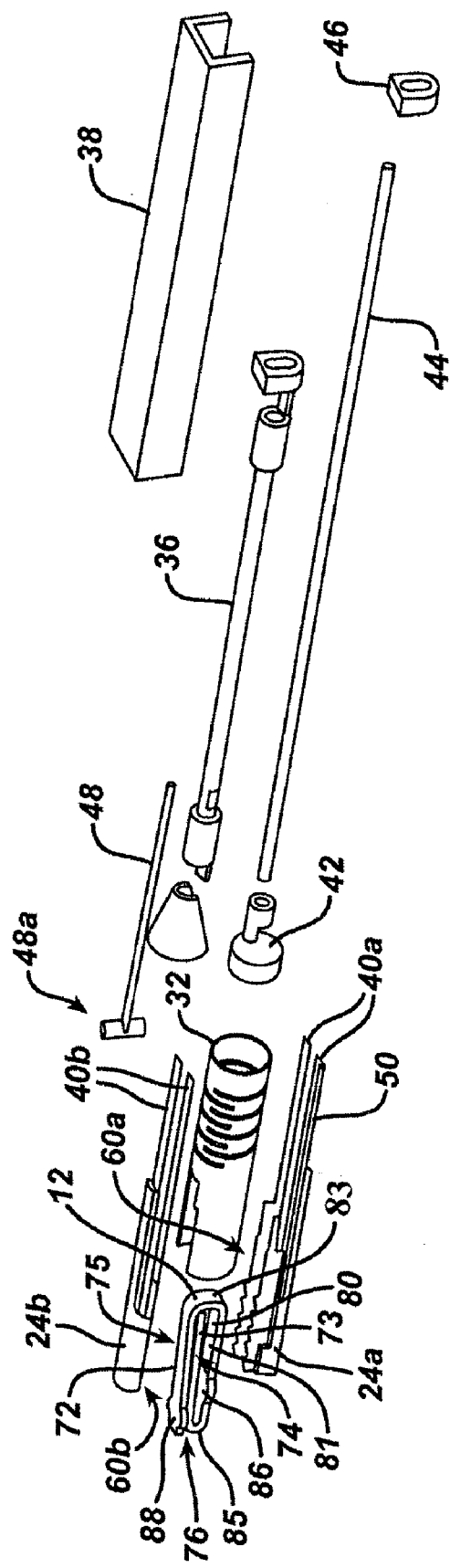
FIG. 3 is an exploded view of a distal portion of the clip applying device of FIG. 1.

The trigger handle 18 includes a trigger arm extending from the housing 14 so that a user of the device 10 can hold the stationary handle 16 and actuate the trigger handle 18 by grasping the trigger handle arm with the same hand. Posts 30, molded into the trigger handle 18 and/or molded in the housing 14, the stationary handle 16, and/or a coupling mechanism 52 and configured to fit into holes formed in the trigger handle 18, can allow pivotal movement of the trigger handle 18 with respect to the stationary handle 16. The coupling mechanism 52 can be disposed in the housing 14, pivotably coupled to the housing 14, and slidably attached to the trigger handle 18 and can be configured to couple the force applied to the trigger handle 18 to the tissue grasping/compressing and clip advancing/placing functions of the device 10. FIG. 1 shows the trigger handle 18 in a closed position following closure of the jaws 24 and deployment of the clip 12 from the distal end 22 of the device 10, and FIG. 2 shows the trigger handle 18 in an open, initial position. Movement of the trigger handle 18 and effectuated movement of other elements of the device 10 is discussed in more detail below.

At least a portion of each of the inner tube 20, the outer tube 26, and the clip applying mechanism 28 can compose a flexible, elongate shaft 58 that extends from a proximal end of the housing 14. A person skilled in the art will appreciate that having a flexible shaft indicates that at least a portion of the shaft 58 is composed of one or more flexible materials. In an exemplary embodiment, the shaft 58 can be composed of a flexible material to allow the portion of the device 10 inserted into a body to flex and to be insertable into a body through a flexible introducer device as discussed further below. The material(s) used to form the shaft 58 can be selected so that shaft 58 can deliver any amount of push-pull force at the distal end 22 of the device 10 without deforming, where deformation can make the business end of the device 10 harder to control and more likely to unintentionally stray from a desired surgical location. In an exemplary embodiment, the shaft 58 can deliver about 15 pounds of push-pull force without deforming. The material(s) used to form the shaft 58 can also help the shaft 58 have any radius of curvature without the shaft 58 breaking. In an exemplary embodiment, the shaft 58 can achieve a radius of curvature of about 3 inches.

The shaft 58 can have any size, shape, and configuration. In an exemplary embodiment, the shaft 58 can be substantially cylindrical and be non-coiled, e.g., have a non-coiled outside surface. The shaft 58 can have a uniform or non-uniform diameter along its longitudinal length. In an exemplary embodiment, a maximum diameter of the shaft 58 can be about 1 mm (when the jaws 24 are in a closed position), which can allow the shaft 58 to be advanced through a device channel, natural orifice, body incision, etc. having a diameter greater than about 1 mm. In some embodiments where the shaft 59 has a maximum diameter of the shaft 58 of about 1 mm, when the jaws 24 are in an open position, the maximum diameter of the shaft 58 may exceed 1 mm.

FIGS. 3-7 illustrate a distal portion of the device 10 in more detail. As shown, the outer tube 26, the inner tube 20, and the clip applying mechanism 28 each include a plurality of parts configured to be coupled together, but any one or more of the outer tube 26, the inner tube 20, and the clip applying mechanism 28 can include more or fewer parts than those illustrated in this embodiment. Generally, the outer tube 26 can be fixed with respect to the housing 14, and the inner tube 20 and the clip applying mechanism 28 can each be movable with respect to the housing 14 and the outer tube 26, e.g., axially movable parallel to a longitudinal axis A of the device 10.

The ligating clip disposed within the device 10 can have a variety of configurations. One embodiment of a ligating clip is described in commonly-owned U.S. Pat. Nos. 5,681,330 and 5,601,573, which are hereby incorporated by reference in their entireties. As illustrated in the embodiment in FIG. 3, the ligating clip 12 can include an upper biased leg member 72, a connector portion 80, and a lower biased leg member 73. The upper leg member 72 is located at one end of the clip 12 and the lower leg member 73 is located at opposite free ends of the clip 12, with the connecter portion 80 extending between the upper and lower leg members 72, 73. Each of the upper leg member 72, lower leg member 73, and connector portion 80 can have substantially the same length. The clip 12 can have a folded, traditional paper-clip like configuration where the upper and lower leg members 72, 73 are folded over the connector portion 80 such that the lower leg member 73 is located between the upper leg member 72 and the connector portion 80. The connector portion 80 can include an elongated portion 81 and first and second spring members 83, 85. The first spring member 83 is located in a proximal portion of the clip 12 and is coupled to a proximal portion of the upper leg member 72. The second spring member 85 is located in a distal portion of the clip 12 and is coupled to a distal portion of the lower leg member 73. The upper and lower leg members 72, 73 can be configured to be substantially parallel to each other along substantially their entire lengths when the clip 12 is in a closed position, at least prior to the clip 12 being clipped around tissue, and to not be substantially parallel to each other along substantially their entire lengths when the clip 12 is in an open position. The leg members 72, 73 can be substantially rigid such that when the clip 12 is in the closed position or the open position, the leg members 72, 73 are substantially linear along their respective lengths. Each leg member 72, 73 has an opposed, first and second inner tissue ligating surface 74, 75, respectively. Each tissue ligating surface can interface with the tissue engaging surface of the other leg member. The tissue ligating surfaces 74, 75 can include scored surfaces to help hold tissue between the interfacing surfaces and prevent tissue from slipping out. The tissue ligating surfaces 74, 75 can additionally or alternatively each have a gripping mechanism, e.g., dimples, to help ensure closure and prevent movement of the clip 12 when it is placed around tissue. The proximal ends of the upper and lower leg members 72, 73 can be configured to form a clip opening 76 for capturing a tissue. The upper leg member 72 can include upper transverse tabs 88 located in a distal portion of the upper leg member 72. The connector portion 80 can include lower transverse tabs 86 located in a distal portion of the connector portion 80.

The outer tube 26 at its proximal end includes a clip feeder support member 56 configured to help stabilize the clip applying mechanism 28 and to provide a stop for a knob 54 of the inner tube 20. The outer tube 26 also includes the jaws 24, a jaw casing 32 configured to have the clip 12 removably disposed therein with the clip 12 in a closed position (see FIG. 5) and configured to allow the jaw members 24a, 24b to be pivotably mounted thereto, a proximal jaw casing 34 configured to be coupled to a proximal end of the jaw casing 32, a first support tube 36 configured to be coupled to a proximal end of the proximal jaw casing 34, and a base beam 38 configured to be coupled to the first support tube 36 and to provide a stabilizing force to at least the portion of the device 10 distal to the base beam 38.

Figure 6:
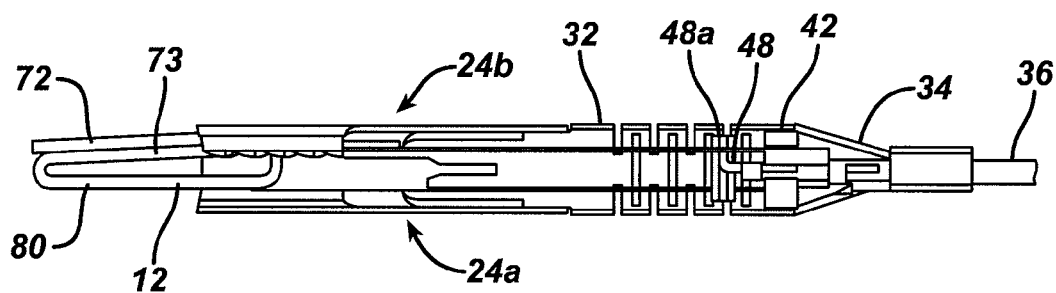
FIG. 6 is a side schematic view of the clip applying device of FIG. 5 with the device's jaws in a closed position and the clip advanced partially through the jaws.
Figure 7:
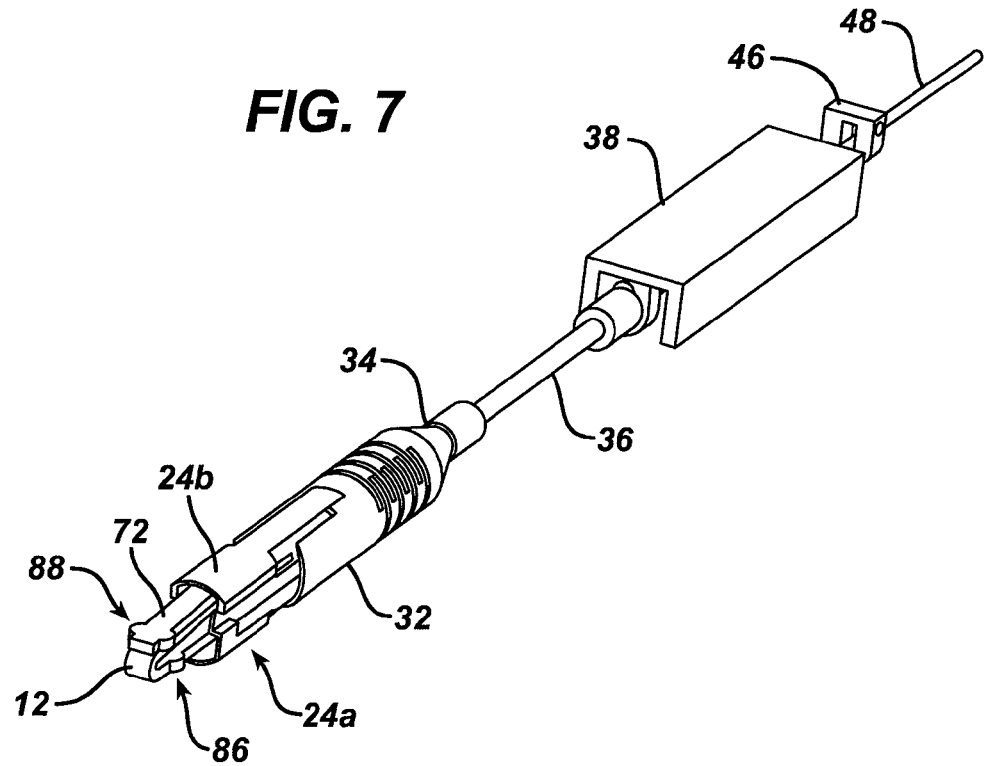
FIG. 7 is a perspective view of the clip applying device of FIG. 6.

The jaws 24 can be configured to be movable to allow tissue to be clamped between opposed, lower and upper tissue clamping surfaces 60a, 60b of the respective jaw members 24a, 24b. The tissue clamping surfaces 60a, 60b can be textured, e.g., have interlocking, substantially triangular teeth (as shown), to help grip tissue therebetween. The pivotal mounting of the jaw members 24a, 24b to the jaw casing 32 can allow the jaw members 24a, 24b to move between open and closed positions relative to the device's longitudinal axis A. FIGS. 4, 6, and 7 illustrate the jaws 24 in an open position, and FIGS. 1 and 5 illustrates the jaws 24 in a closed position. The jaws 24 can be biased to the open position such that when the device 10 is in an initial, resting position, the jaws 24 are in the open position.

Figure 23:
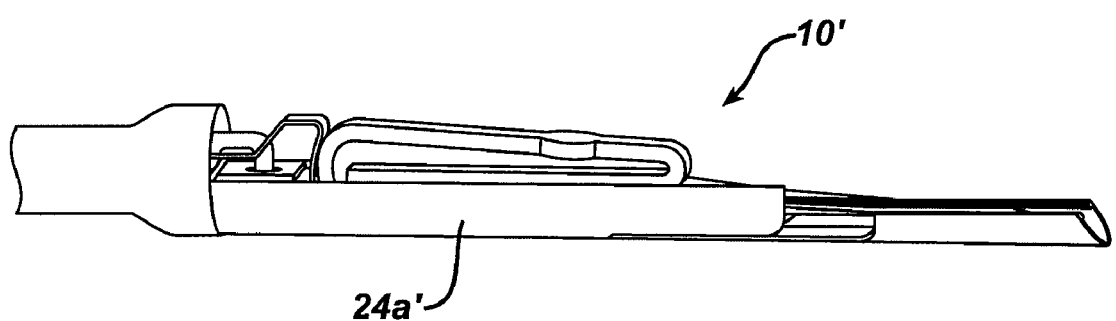
FIG. 23 is a partial schematic view of a distal portion of an embodiment of a clip applying device having one movable jaw member and one stationary jaw member.

Although the device 10 is illustrated as having two movable jaw members, the jaws 24 can include more than two jaw members. Furthermore, the device 10 can have one moveable jaw member and one stationary jaw member, as will be appreciated by a person skilled in the art. FIG. 23 shows one embodiment of a clip applying device 10' having a stationary lower jaw member 24a' at the device's distal end. (The movable upper jaw member is not illustrated on the device 10'.) The clip applying device 10' also illustrates an alternate embodiment of a shoe 48a' configured as a molded bar.

Referring again to FIGS. 1-7, the jaws 24 can be configured to engage the clip 12 when the clip 12 is distally advanced through the device 10 to help pry open the clip 12 to allow the clip 12 to be positioned around tissue to be ligated. In an exemplary embodiment, the jaw members 24a, 24b have c-shaped cross-sections, although the jaw members 24a, 24b can each have any cross-sectional shape. A lower longitudinal channel can be formed in the lower jaw member 24a through which a downwardly extending portion of the shoe 48a of the feed bar 48 can ride to help ensure the proper placement of the distal end of the feed bar 48 with respect to the clip 12 throughout clip advancement and placement. An upper longitudinal channel can be similarly formed in the upper jaw member 24b through which an upwardly extending portion of the shoe 48a can ride. When the clip 12 is pushed in a distal direction by the feed bar 48, the lower transverse tabs 86 on the lower biased leg member 73 of the clip 12 can be configured to ride on a sloped surface, e.g., shelves, formed in side walls of the lower jaw 24a. The shelves can interface with an inner surface of the lower transverse tabs 86. The upper transverse tabs 88 on the connector portion 80 of the clip 12 between the upper and lower biased leg members 72, 73 can be configured to ride along a sloped surface, e.g., ramps, formed in the lower jaw member 24a. The ramps can be configured to engage inner surfaces of the upper tabs 88 and angle the upper tabs 88 towards the upper jaw member 24a, causing the opposed, first and second inner tissue ligating surfaces 74, 75 of respective biased leg members 72, 73 to separate from each other to provide the clip opening 76. At the end of the ramps the upper transverse tabs 88 can be configured to make a transition from the lower jaw member 24a to rails in the upper jaw member 24b. The rails can be configured to engage the inner surface of the upper transverse tabs 88. Thus, the first tissue ligating surface 74 of the upper leg member 72 can be advanced into the upper jaw member 24b above a tissue compressed between the jaw members 24a, 24b. The second tissue ligating surface 75 of the lower leg member 73 can be advanced into the lower jaw member 24a below the compressed tissue.

Throughout the advancement of the clip 12, the body of the clip 12 can be contained within the longitudinal channels in the jaw members 24a, 24b. The upper jaw member 24b can include rails configured to engage a portion of the clip 12, and the lower jaw member 24a can include shelves configured to engage another portion of the clip 12. The upper tabs 88 can advance to an opening towards the distal end of the upper jaw member 24b. The width of the opening can be greater that the inner width of the rails and closely correspond to the outside width of the upper tabs 88. The upper tabs 88 can disengage from the upper jaw member 24b as they are advanced through the opening, thereby allowing the upper leg member 72 to resiliently move toward the lower leg member 73 and contact a tissue clamped in the jaws 24 with the first tissue ligating surface 74.

Likewise, at approximately the same time, the lower transverse tabs 86 can reach an opening towards the distal end of the lower jaw member 24a. The width of the opening can be greater that the inner width of the shelves and closely correspond to the outside width of the lower transverse tabs 86. This can allow the lower tabs 86 to disengage from the lower jaw member 24a through the opening, thereby allowing the lower leg member 73 to resiliently move toward the upper leg member 72 and contact tissue with the second tissue ligating surface 75. The position of the tabs 86, 88 can correspond to the timing of leg member disengagement from the jaws 24 to help correctly place the clip 12 on a tissue. Although an upper and lower set of transverse tabs are shown, a person skilled in the art will appreciate that a number of combinations, including a single tab alone, are possible for disengaging a clip from the instrument.

The inner tube 20 at its proximal end includes the knob 54, which is coupled to the distal end of the housing 14 and configured to be movable, e.g., longitudinally moveable parallel to the longitudinal axis A, to move the jaws 24 between the open and closed positions. Generally, pulling the knob 54 in a proximal direction can close the jaws 24, while pushing the knob 54 in a distal direction can open the jaws 24. The knob 54 can also be configured to be rotatable to permit any degree of rotation, e.g., 360 degree rotation, of at least the shaft 58 with respect to the housing 14. The inner tube 20 also includes a jaw feeder including lower and upper jaw feeders 40a, 40b configured to couple to the jaws 24 and to respectively move the lower and upper jaw members 24a, 24b between the open and closed positions, a clip feeder casing 42 configured to couple to a distal end of the jaw feeders 40a, 40b, a second support tube 44 configured to couple to a proximal end of the clip feeders casing 42 and to be disposed within a lumen extending through the first support tube 36, and a distal support member 46 configured to couple to a proximal end of the second support tube 44 and to provide a stabilizing force to the clip applying mechanism 28.

The clip applying mechanism 28 includes a feed bar 48 configured to be disposed within a lumen extending through the second support tube 44. A distal end of the feed bar 48 can have a shoe 48a formed thereon or coupled thereto to help push the clip 12 through the jaw casing 32 and out the device's distal end 22. The shoe 48a can also help provide a stop for the clip applying mechanism 28 against the clip feeder casing 42 when the feed bar 48 moves in a proximal direction. A proximal end of the feed bar 48 can include a pusher button 48b disposed within the clip feeder support member 56 and configured to engage the coupling mechanism 52 such that movement of the coupling mechanism 52 can translate to movement to the feed bar 48, as discussed further below. The clip applying mechanism 28 also includes a feed bar support member 50 configured to receive the clip 12 thereon within the jaw casing 32.

Figure 8:
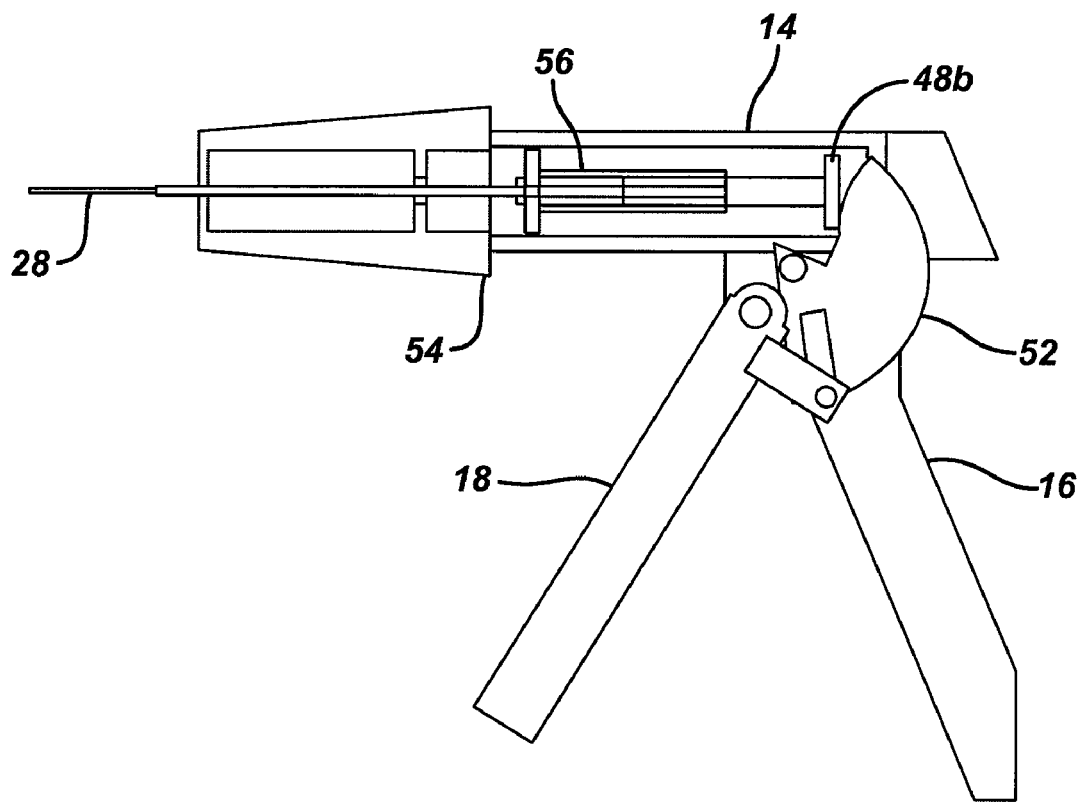
FIG. 8 is a partial schematic, cross-sectional view of the clip applying device of FIG. 1 with the device's trigger handle in an initial position.

FIGS. 8-19 illustrate one embodiment of a ligating clip applying device, e.g., the device 10, in use. As mentioned above, when the device 10 is in an initial, resting position, the jaws 24 can be in the open position. In some embodiments the jaws 24 can be inserted into a body of a patient in an open position, but in an exemplary embodiment, the jaws 24 are in a closed position when introduced into a body to help reduce the diameter of the device's distal end during device introduction into the body and to help reduce chances of the jaws 24 catching on or harming any material the jaws 24 pass en route to a desired surgical site. The jaws 24 can be closed in any way, such as by pulling the knob 54, e.g., toward the housing 14 as shown in FIG. 8, to move the jaws 24 from the open position to the closed position.

Figure 9:
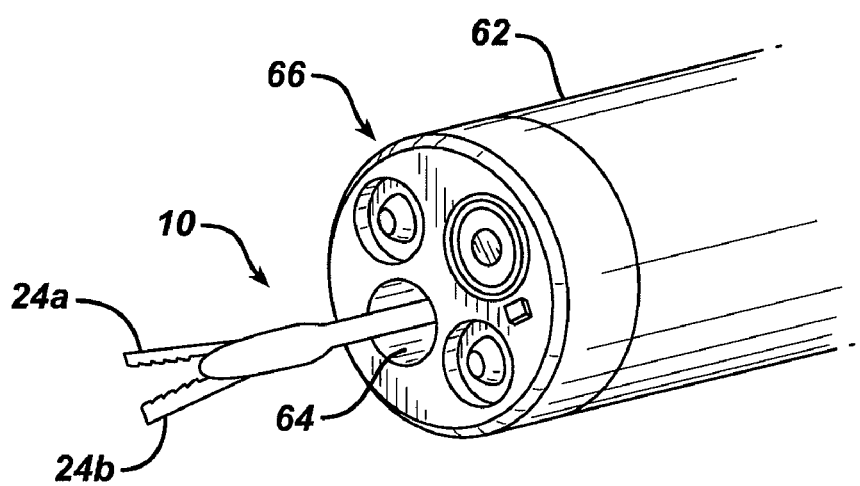
FIG. 9 is a perspective view of the clip applying device of FIG. 1 disposed in a working channel of an endoscope.

With the jaws 24 in their desired position, the device 10 in a pre-inserted position can be introduced into a body in any way appreciated by a person skilled in the art, e.g., through a natural orifice with or without assistance of an introducer device (e.g., a scoping device, a trocar, etc.), through a bodily incision, etc. In an exemplary embodiment, the device 10 can be introduced distal end 22 first into a body of a patient through a working channel 64 of an endoscope 62, as illustrated in FIG. 9. The endoscope 62 can be advanced into the body with or without the device 10 disposed within the working channel 64, although in an exemplary embodiment, whether the device 10 is disposed in the working channel 64 during advancement of the endoscope 62 through the body or not, the device's distal end 22 does not extend beyond the endoscope's distal end 66 until the endoscope 62 has been positioned adjacent a desired surgical site to help reduce chances of the device 10 catching on or harming any material the exposed portion of the device 10 passes en route to the desired surgical site.

When the device 10 has been advanced a sufficient distance through the endoscope 62 such that the jaw members 24a, 24b extend beyond a distal end 66 of the endoscope 62, the jaws 24 can be configured to "spring" from the closed position to the open position since the jaws 24 can be biased to an open position. Depending on whether the jaws 24 are configured to be locked in the closed position when manually closed by pulling the knob 54 and depending on the available space within the working channel 64 and the diameter of the portion of the device 10 advanced through the working channel 64, the jaws 24 may be configured to move toward the open position while disposed within the working channel 64 but not be fully open and thus still be considered to be in the closed position within the working channel 64. If the jaws 24 are not configured to automatically be in the open position following their advancement beyond the endoscope's distal end 66, the jaws 24 can be moved to the open position in another way, e.g., through handle actuation, through pushing the knob 54, etc., so that the jaws 24 can clamp tissue therebetween.

Figure 10:
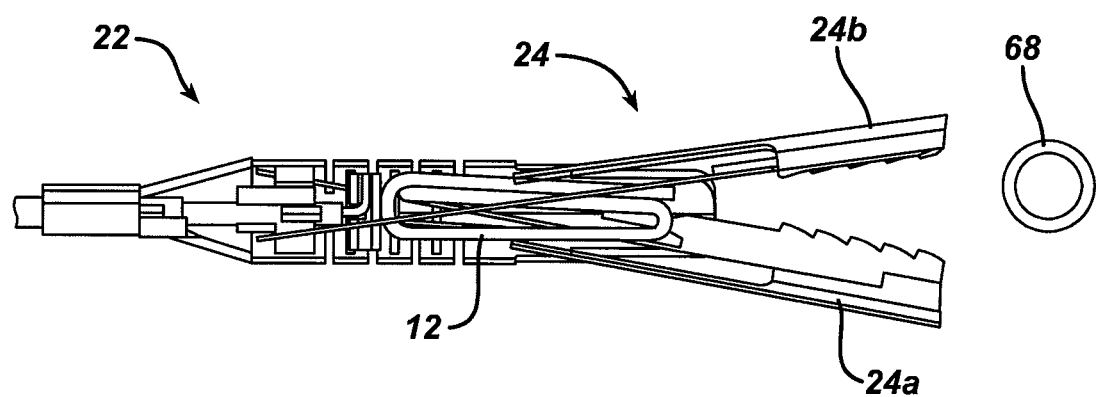
FIG. 10 is a side cross-sectional view of a distal portion of the clip applying device of FIG. 1 positioned adjacent a blood vessel to be ligated using the ligating clip disposed in the device.
Figure 11:
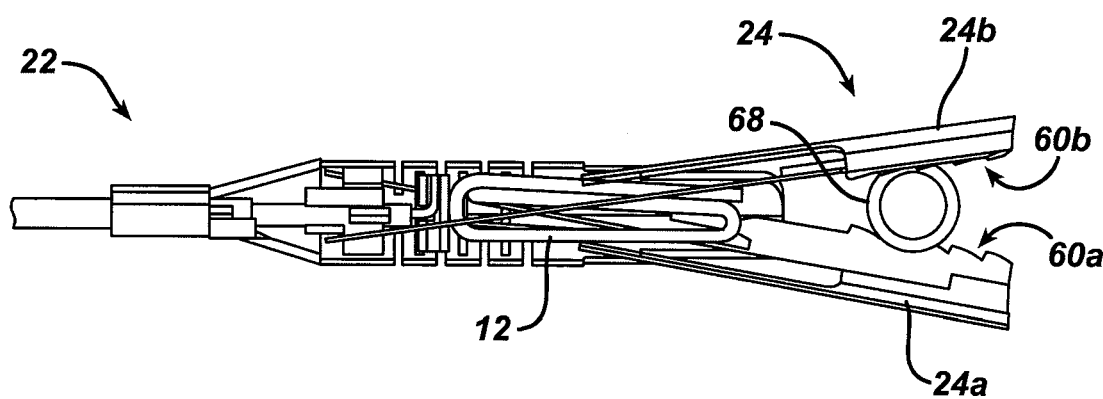
FIG. 11 is a side cross-sectional view of the device of FIG. 10 with the blood vessel placed between the device's jaws.
Figure 12:
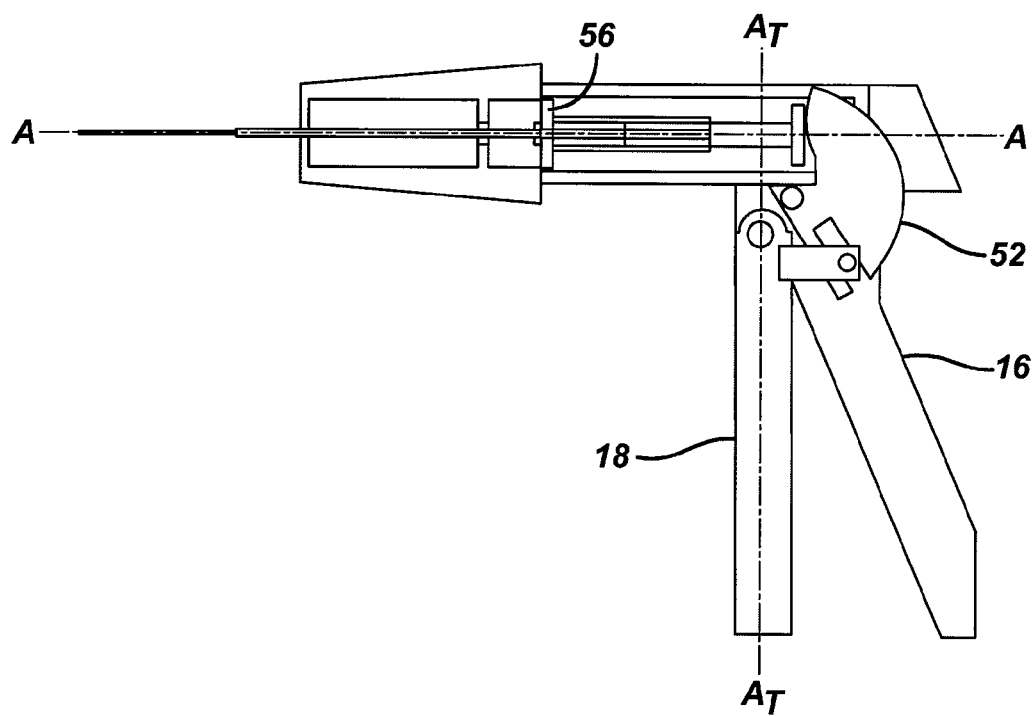
FIG. 12 is a partial schematic, cross-sectional view of the clip applying device of FIG. 8 with the device's trigger handle moved to a first actuated position.

Inside the body, as illustrated in FIG. 10, the distal end 22 of the device 10 can be positioned at a surgical site adjacent a tissue, e.g., a vessel 68, to be ligated using the clip 12 disposed within the device 10. Although the jaws 24 are shown in the open position in FIG. 10, the device 10 can be positioned adjacent the vessel 68 with the jaws 24 open or closed.

Figure 13:
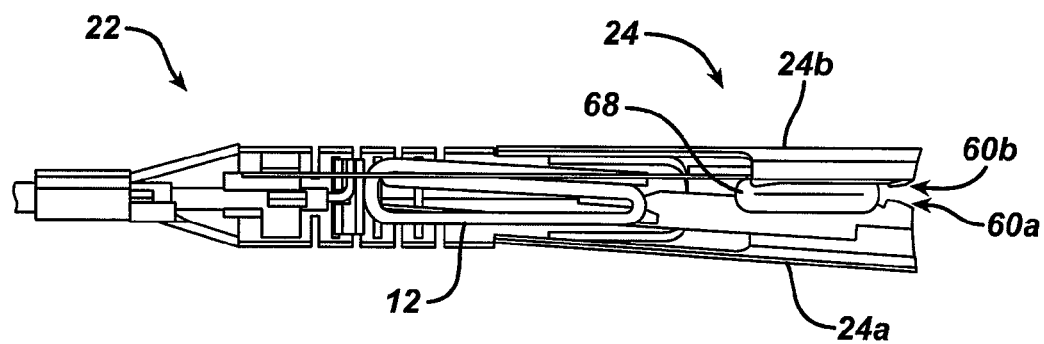
FIG. 13 is a side cross-sectional view of the device of FIG. 11 with the blood vessel compressed between the device's jaws.
Figure 14:
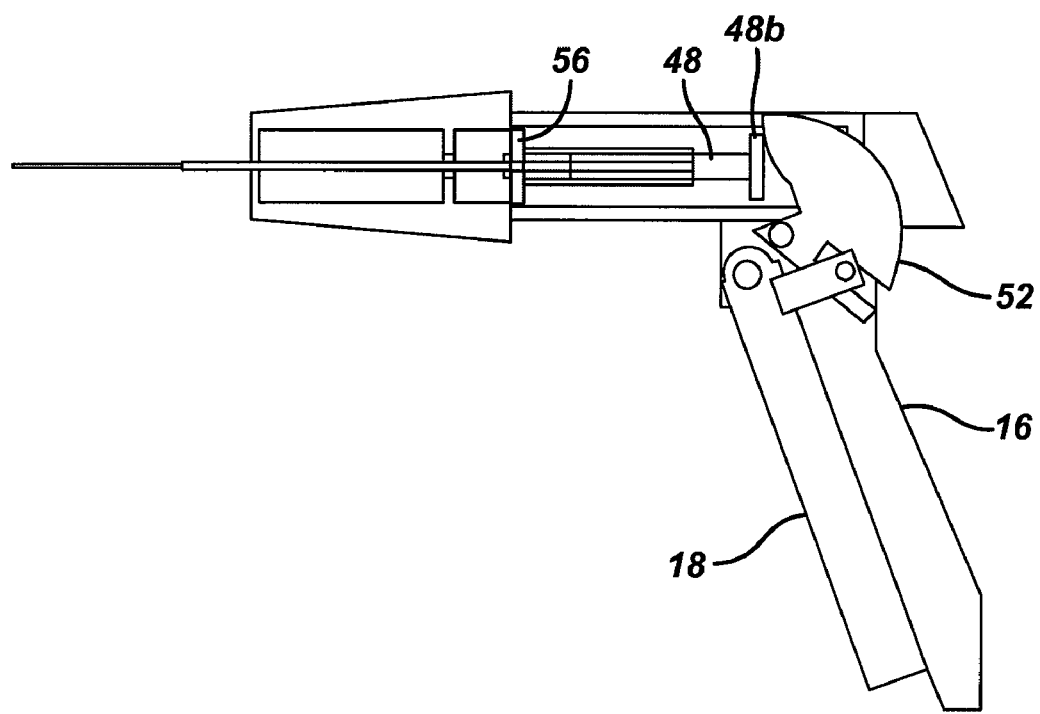
FIG. 14 is a partial schematic, cross-sectional view of the clip applying device of FIG. 12 with the device's trigger handle moved to a second actuated position.

With the jaws 24 in the open position, the jaw members 24a, 24b can be positioned about the vessel 68, as shown in FIG. 1, such that the vessel 68 is positioned between the jaws' tissue contacting surfaces 60a, 60b. However, when positioned between the jaw members 24a, 24b, the vessel 68 does not necessarily contact the tissue contacting surfaces 60a, 60b until the jaws 24 move from the open position. The trigger handle 18 can be actuated in a first actuating stroke from an initial position shown in FIG. 8 to a first actuated position illustrated in FIG. 12 to move the jaws 24 from the open position to the closed position, thereby clamping the vessel 68 between the jaws' tissue contacting surfaces 60a, 60b, as illustrated in FIG. 13.

The trigger handle 18 can be pulled toward the stationary handle 16 to rotate the trigger handle 18 from the initial position to the first actuated position. Moving from the initial position to the first actuated position, the trigger handle 18 can cause the coupling mechanism 52 to rotate counter-clockwise and push the pusher button 48b, thereby translating force from movement of the trigger handle 18 to the pusher button 48b. As the coupling mechanism 52 rotates and pushes the pusher button 48b, the clip applying mechanism 28 can move a first distance axially in a distal direction, thereby also moving the clip feeder support member 56 to which it is coupled within the housing 14. The clip feeder support member 56 can thus move distally until a distal end of the clip feeder support member 56 abuts the knob 54. A user of the device 10 can know that that the trigger handle 18 has moved from the initial position to the first actuated position through visual verification of the handle's position, by feeling a force imparted to a user when the clip feeder support member 56 abuts the knob 54, and/or by viewing the jaws 24 at the surgical site directly and/or through remote imaging technology as will be appreciated by a person skilled in the art. In the first actuated position, a longitudinal axis AT of the trigger handle 18 can be substantially orthogonal to the longitudinal axis A of the device 10.

With the jaws 24 clamped around the vessel 68, the clip 12 can be advanced from the device 10 to clip around and ligate the vessel 68. To advance the clip 12 out of the device 10 and around the vessel 68, the trigger handle 18 can be moved in a second actuating stroke from the first actuated position to a second actuated position illustrated in FIG. 14. Rotating from the first actuated position to the second actuated position, the trigger handle 18 can cause the coupling mechanism 52 to rotate counter-clockwise and push the pusher button 48b, similar to that discussed above, to advance the clip 12 into the jaw members 24a, 24b which have closed over, compressed, and temporarily occluded the vessel 68. The feed bar 48 can distally, axially advance through a lumen formed in the clip feeder support member 56, thereby causing the shoe 48*a* to push the clip 12 into and through the jaws 24 and to push the clip 12 beyond a distal end of the device 10 with the vessel 68 clipped by the clip 12.

Figure 15:
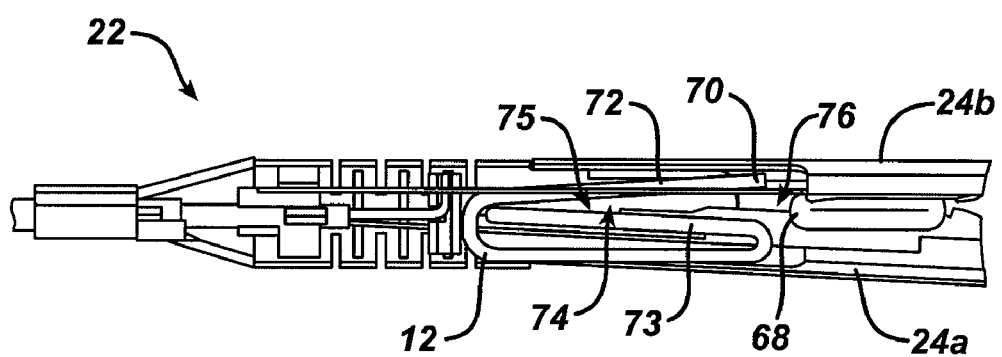
FIG. 15 is a side cross-sectional view of the device of FIG. 13 with the ligating clip approaching the blood vessel compressed between the device's jaws.
Figure 16:
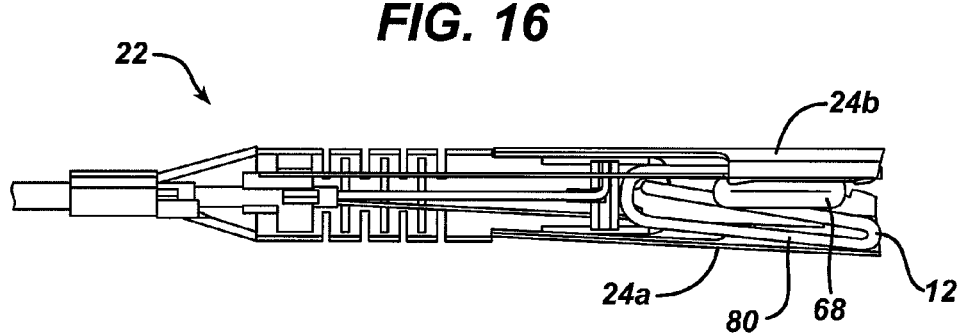
FIG. 16 is a side cross-sectional view of the device of FIG. 15 with the ligating clip positioned around the blood vessel.
Figure 17:
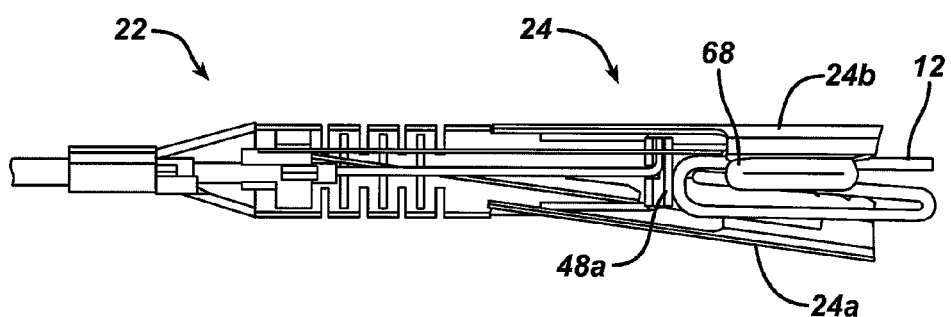
FIG. 17 is a side cross-sectional view of the device of FIG. 16 with the ligating clip clipping the blood vessel.
Figure 18:
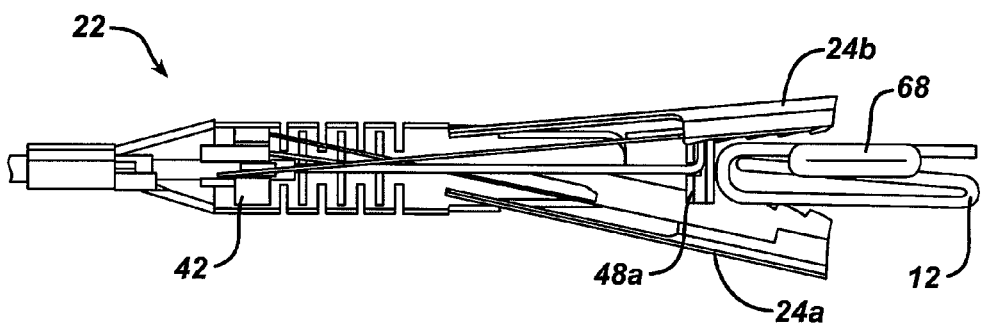
FIG. 18 is a side cross-sectional view of the device of FIG. 17 with the ligating clip clipping the blood vessel and being deployed from the device.

FIGS. 15-18 illustrate movement of the clip 12 during movement of the trigger handle 18 from the first actuated position to the second actuated position. As shown in FIG. 15, the clip 12 sits just proximally of the vessel 68 compressed by the jaw members 24*a*, 24*b* just after the first portion of the distal advancement of the feed bar 48 occurs while moving the trigger handle 18 from the first actuated position to the second actuated position. A distal end 70 of a first leg member 72 of the clip 12 can ride up ramps to the upper jaw 24*b*, separating tissue ligating surfaces 74, 75 of the clip's biased leg members 72, 73, which are biased to a closed position, from each other to provide an opening 76. In FIG. 16, the clip 16 is advanced over the vessel 68 with the clip's first leg member 72 engaging the rails in the upper jaw member 24*b* and the clip's connector portion 80 interfacing with the shelves in the lower jaw member 24*a*. FIG. 17 shows the clip 12 beginning to disengage from the jaws 24 and extend beyond a distal end of the device 10. In FIG. 18, the clip 12 is disengaged from the shelves, the rails, and the jaws 24 at the distal end 22 of the device 10, thereby allowing the clip 12 to "spring" to its biased closed position and clip tissue between its tissue ligating surfaces 74, 75. This positioning in FIG. 18 corresponds to the trigger handle 18 being in the second actuated position shown in FIG. 14.

Figure 19:
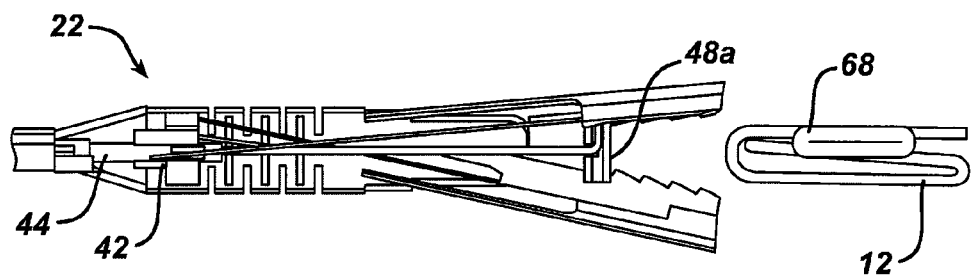
FIG. 19 is a side cross-sectional view of the device of FIG. 18 with the ligating clip clipping the blood vessel and disengaged from the device.

When the clip 12 is disengaged from the device 10 and the trigger handle 18 is released, the trigger handle 18 can return to its initial position illustrated in FIG. 8. FIG. 19 shows the clip 12 positioned around the vessel 68 and disengaged from the device 10 at a position completely distally beyond the device's distal end.

The device 10 can be withdrawn from the surgical site at any time. When the device 10 is pulled proximally into the endoscope 62, the walls of the working channel 64 can apply a force to the jaws 24 to move the jaws 24 from the open position to the closed position for the jaws' movement through the working channel 64. Instead or in addition to being configured for such automatic closure in preparation for travel through the endoscope 62, the jaws 24 can be configured to be manually closed, such as through manipulation of the knob 54.

A clip applying device can be configured similar to the device 10 described above but have a plurality of ligating clips disposed therein. The device can sequentially position and deploy each of the clips in a manner similar to that described above. The plurality of clips can be pre-loaded as a stack into the device in an end to end configuration along a longitudinal axis of the device's shaft, such as by removably mounting clips 110 on a feed bar 112, as shown in an embodiment in FIG. 24, configured to be disposed in a clip applying device shaft. An embodiment of such a stack and sequential deployment is described in commonly-owned U.S. Pat. Nos. 5,681,330 and 5,601,573, both mentioned above, and in commonly-owned U.S. Pat. No. 7,090,685, which is hereby incorporated by reference in its entirety.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a flexible shaft configured to be advanced through a flexible scoping device and to have a ligating clip in a closed position removably disposed therein, the shaft comprising
   an outer tube with jaws at a distal end thereof, the jaws configured to move between open and closed positions,
   an inner tube disposed within the outer tube and configured to be movable to move the jaws between the open and closed positions, and
   a clip applying mechanism disposed within the inner tube and configured to be movable to advance the ligating clip beyond a distal end of the shaft, wherein the ligating clip is configured, subsequent to the jaws moving from the open position to the closed position so as to compress tissue therebetween, to move to a closed position, clip the tissue, and be advanced beyond the distal end of the shaft with the jaws being in the closed position.

2. The device of claim 1, wherein the shaft is composed of at least one of a shape memory material, stainless steel, and spring steel.

3. The device of claim 2, wherein the shaft is composed of a superelastic material.

4. The device of claim 1, further comprising a handle coupled to the shaft and configured to be actuated to move the inner tube and to move the clip applying mechanism.

5. The device of claim 4, wherein the handle is configured to be actuated in a first actuating stroke to move the inner tube and in a second actuating stroke after the first actuating stroke to move the clip applying mechanism.

6. The device of claim 5, wherein the first actuating stroke moves the jaws from the open position to the closed position, thereby causing tissue to be compressed between tissue compressing surfaces of the jaws, and wherein the second actuating stroke advances the ligating clip over the tissue compressed between the tissue compressing surfaces to allow the ligating clip to move to the closed position to clip the tissue therebetween.

7. The device of claim 1, wherein the inner tube is configured to be axially movable with respect to the outer tube.

8. The device of claim 1, wherein the shaft is non-coiled.

9. The device of claim 1, wherein the shaft can deliver any amount of push-pull force without deforming.

10. The device of claim 1, wherein the shaft can achieve any radius of curvature without the shaft breaking.

11. The device of claim 1, wherein the shaft has a maximum diameter not greater than 1 mm.

12. The device of claim 1, wherein the ligating clip is configured to advance through the jaws and to spring to the closed position to clip tissue when advanced beyond a distal end of the jaws.

13. The device of claim 1, wherein the shaft is configured to have a plurality of ligating clips disposed therein, each of the plurality of ligating clips disposed therein in a closed position and configured to move from the closed position to an open position and back to the closed position to clip tissue when advanced beyond the distal end of the shaft and when the jaws are in a closed position, wherein the clip applying mechanism is configured to sequentially advance each of the plurality of clips beyond the distal end of the shaft.

14. The device of claim 13, further comprising a plurality of ligating clips removably disposed in the shaft, each of the plurality of ligating clips disposed therein in a closed position.

15. The device of claim 14, wherein each of the ligating clips has transverse tabs extending therefrom, and the jaws each have a sloped surface formed therein, the sloped surfaces being configured to engage the transverse tabs and pry open the closed ligating clips when each of the closed ligating clips is advanced into the jaws.

16. The device of claim 1, further comprising a ligating clip removably disposed in the shaft in a closed position.

17. The device of claim 16, wherein the ligating clip removably disposed in the shaft in the closed position is configured to move from the closed position to an open position and back to the closed position to clip tissue before being advanced distally beyond the distal end of the shaft.

18. The device of claim 16, wherein the ligating clip has transverse tabs extending therefrom, and the jaws each have a sloped surface formed therein, the sloped surfaces being configured to engage the transverse tabs and pry open the closed ligating clip when the closed ligating clip is advanced into the jaws.

19. The device of claim 1, wherein the outer tube comprises a first elongate tubular member, the inner tube comprises a second elongate tubular member disposed within the first elongate tubular member, and the inner tube comprises a knob at a proximal end thereof, the knob being configured to move relative to the outer tube to move the jaws between the open and the closed positions.

20. The device of claim 19, wherein the outer tube comprises a support member coupled to the clip applying mechanism configured to move distally with the clip applying mechanism relative to the knob until a distal end of the support member abuts the knob.

21. The device of claim 20, further comprising a handle coupled to the shaft, the handle being configured to be actuated in an actuating stroke to move the clip applying mechanism and the support member distally until the distal end of the support member abuts the knob.

\* \* \* \* \*